United States Patent [19]

Damien

[11] Patent Number: 4,942,870

[45] Date of Patent: Jul. 24, 1990

[54] DENTAL HYGIENE DEVICE

[76] Inventor: George Damien, 3631 U.S. 19 N., Palm Harbor, Fla. 34684

[21] Appl. No.: 238,013

[22] Filed: Aug. 29, 1988

[51] Int. Cl.$^5$ .............................................. A61H 9/00
[52] U.S. Cl. .......................................... 128/66; 433/80
[58] Field of Search ................ 128/66, 62 A; 433/80, 433/84, 100; 403/DIG. 4; 285/33

[56] References Cited

U.S. PATENT DOCUMENTS

| | | | |
|---|---|---|---|
| 1,904,061 | 4/1933 | Larsen | 403/DIG. 4 |
| 2,829,645 | 4/1958 | Matteson | 128/62 A |
| 3,227,380 | 1/1966 | Pinkston | 128/62 A |
| 3,273,189 | 9/1966 | Levinson et al. | 128/66 |
| 3,500,824 | 3/1970 | Gilbert | 128/66 |
| 3,669,101 | 6/1972 | Kleiner | 128/66 |
| 4,265,229 | 5/1981 | Rice et al. | 128/66 |
| 4,445,860 | 5/1984 | Oehler | 433/132 |

*Primary Examiner*—Cary E. Stone

*Attorney, Agent, or Firm*—Joseph C. Mason, Jr.; Ronald E. Smith

[57] ABSTRACT

A free-standing oral hygiene device that is attachable to and detachable from a faucet member with one hand. An elongate flexible hose extends from the device to a hand-held wand which terminates in a nozzle that ejects a jet stream of water onto the teeth and gums of the user. When water pressure exceeds an adjustable preselected threshhold, a pressure relief valve opens so that the gums of the individual are not injured. A retaining clip member is depressed when the device is attached to the faucet, and released. When the retaining clip has been released, it holds the device to the faucet even when the water pressure from the faucet is very high. Removing the device is accomplished by depressing the retaining clip a second time and displacing the device downwardly. It can then be stored on a substantially level support surface as a free-standing unit.

14 Claims, 3 Drawing Sheets

DENTAL HYGIENE DEVICE

TECHNICAL FIELD

This invention relates, generally, to dental hygiene devices. More particularly, it relates to a free-standing device that may be quickly attached to and detached from a conventional faucet with one hand. The device directs a jet stream of water from the faucet onto the user's teeth and gums. If the water pressure from the faucet exceeds a predetermined threshold, a pressure relief valve opens to divert water away from the user's teeth and gums.

BACKGROUND ART

It is well known that toothbrushes do not adequately clean teeth because the bristles thereof do not extend between the teeth. Moreover, the bristles are quite abrasive and, thus, do not do a good job of massaging the gums to help keep them healthy. Inventors have therefore developed devices that clean between teeth and which stimulate the gums as well. Some of the devices employ waxed or unwaxed strings known as floss; the floss is placed between the teeth and are used in a well known way. Other inventors, as shown in U.S. Pat. Nos. 3,468,306; 3,499,440; 3,509,874; 3,690,314; 3,771,517; 3,973,558 and 4,135,501, have developed devices that direct a small stream of water between the user's teeth. The water can also be directed against the gums to achieve stimulation.

There is a need for an improved wet flossing means, however. For example, the art lacks a free-standing wet flossing device that can be quickly attached or detached to a conventional faucet means with one hand and which has a pressure relief means that will protect the user if the pressure of the water emanating from the device exceeds a predetermined threshhold.

DISCLOSURE OF INVENTION

The invention includes an adapter member, the upper end of which is screw threadedly secured to a conventional faucet means. The adapter functions as an aerator and therefore remains secured to the faucet even when the invention is not in use.

The main body portion of the inventive apparatus is generally tubular and its upper end slidingly receives the lower end of the adapter.

The upper end of the main body portion defines a broad upper cavity that receives water from the faucet as well as the lower end of the adapter; the broad cavity narrows down to a relatively narrow cavity substantially mid-length of the main body portion and again widens out at the lower half thereof.

A spring loaded pressure relief valve prevents flow of water through the main body portion of the device by seating against the lower end of the narrow medial portion of the cavity formed in the device's main body portion when the pressure exerted by the water from the faucet is less than the pressure exerted by the spring against the pressure relief valve.

When the pressure exerted by the water from the faucet exceeds the pressure exerted by the spring against the pressure relief valve, the spring is compressed and the valve means is driven from its seat and water flows through the main body portion and into the sink through a bore formed centrally of a generally disk shaped, flat bottomed, base member.

The base member includes an integral, upwardly projecting sleeve member that slidingly receives the lower end of the spring member that loads the pressure relief valve means. The lowermost end of the bore formed in the sleeve member has a reduced diameter to support the spring member.

The sleeve member is externally threaded; the lower cavity of the device's main body portion is internally threaded so that relative rotation of the main body portion and the base member adjusts the pressure on the spring member and thus determines the amount of water pressure required to unseat the pressure relief valve.

When the water pressure entering the upper cavity of the main body of the device is less than the pressure exerted by the spring member, water entering the central bore of the main body exits therefrom through a radially disposed passageway of truncate length. The proximal end of an elongate flexible hose member is confluent with the passageway and carries water under pressure to a hollow hand-held wand member confluent with the distal end of the hose member. A small nozzle means formed in the distal end of the wand directs a small jet of water into the spaces between the user's teeth and onto the user's gums.

A novel latch mechanism allows the user of the device to attach it to a faucet with one hand and to detach it from the faucet with one hand as well.

Thus, when the device is in use, it is releasably secured at its uppermost end to the faucet, and when it is not in use, it is disposed in free-standing relation to a suitable support surface.

Moreover, when the pressure exerted by the water from the faucet exceeds the pressure exerted by the spring, the pressure of the water streaming from the nozzle means of the wand is substantially reduced as the pressure relief valve is unseated.

A primary object of this invention is to provide a water flossing means that is free standing when not in use, which is provided with an adjustable pressure relief valve means, and which is quickly and easily attachable and detachable to and from a faucet member.

The invention accordingly comprises the features of construction, combination of elements and arrangement of parts that will be exemplified in the description set forth hereinafter and the scope of the invention will be set forth in the claims.

BRIEF DESCRIPTION OF DRAWINGS

For a fuller understanding of the nature and objects of the invention, reference should be made to the following detailed description, taken in connection with the accompanying drawings, in which.

Similar reference numerals refer to similar parts throughout the several views of the drawings.

BEST MODES OF CARRYING OUT THE INVENTION

Figure 1:
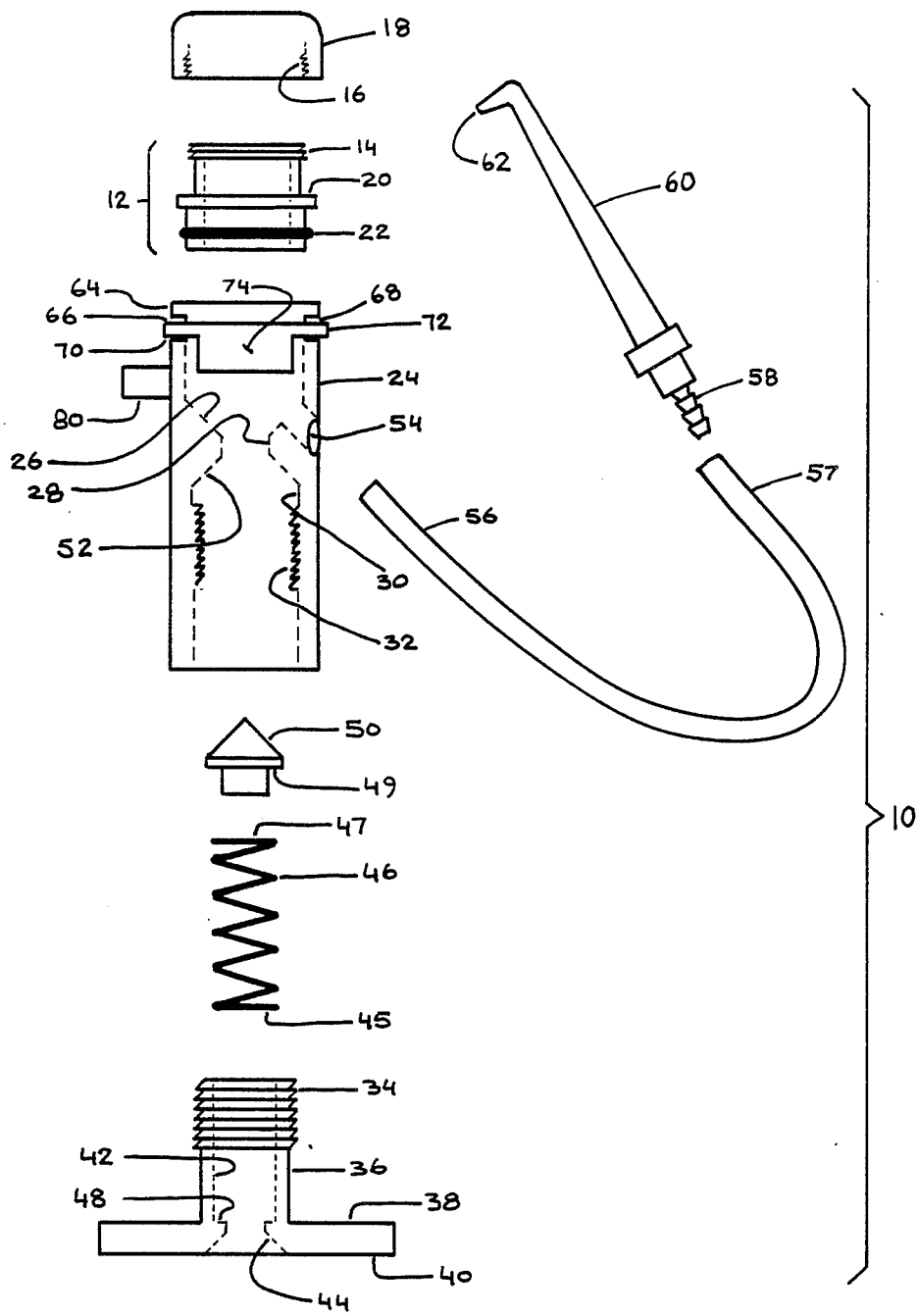
FIG. 1 is an exploded elevational view of the various parts of an apparatus that embodies the invention.

Referring now to FIG. 1, it will there be seen that an embodiment of the novel apparatus that exemplifies the invention is designated by the reference numeral 10 as a whole.

The water flosser 10 is a fluidic device; it includes an adapter member 12 which is provided with external threads 14 which screw threadedly engage internal threads 16 of conventional faucet member 18.

Accordingly, the purchaser of novel device 10 first secures adapter 12 to faucet 18; adapter 12 is provided with a conventional aerator construction so that it may be left in place at all times. Accordingly, since adapter 12 has a central bore, the discharge of water from faucet 18 is not adversely affected when device 10 is not in use.

Adapter 12 includes an annular flange member 20 and an annular O-ring seal means 22, as shown. As will become more clear as this description proceeds, annular flange member 20 provides a stop means which prevents the novel device 10 from disengaging from adapter means 12 when the water pressure within the device is above a level preselected as hereinafter described by the user of the invention.

The main body portion of device 10 is denoted 24 in the drawings. Main body portion 24 has an internal bore, as shown, which bore includes top portion 26, a constricted medial portion 28 and a lower portion 30 having annular internal threads 32 formed therein as shown. When device 10 is fully assembled, threads 32 engage external thread members 34 which are formed in the upwardly projecting sleeve member 36 of annular base member 38. Moreover, when the device is fully assembled, adapter 12 is slidingly received within cavity 26 as suggested by FIG. 1.

Base member 38 has a lower portion that is preferably disk shaped and which has a flat bottom surface 40. Sleeve member 36 is integrally formed with base member 38 and has a central bore 42; the lower portion of base member 38 is bored as at 44.

The lowermost end 45 of spring member 46 is supported by a radially inwardly directed shelf means 48 formed at the intersection of bore means 42 and 44, as shown, when spring member 46 is positioned within bore means 42.

The uppermost end 47 of spring 46 abuts annular shelf means 49 formed in valve member 50 when the device is assembled.

Valve member 50 seats against annular beveled surface 52 formed in the main body portion 24 of device 10 when the device is assembled and when the pressure of water discharged by faucet 18 does not overcome the resistance of spring 46.

Water entering cavity 26 escapes therefrom through passageway 54 and enters elongate flexible tube 56 which is securely fastened at its proximal end to radially projecting passageway 54 so as to be in fluid communication with it. The distal end 57 of tube 56 is securely fastened to the proximal end 58 of a wand means 60 which has a nozzle means 62 formed in the distal end thereof. Water is discharged by nozzle means 62 as long as faucet 18 is discharging water.

To use device 10, its user lifts it from its support surface and attaches it to adapter means 12. Water is turned on in the conventional manner and flows from faucet 18, through adapter 12, and into cavity 26 of the main body portion 24 of device 10. Water is prevented from entering lower cavity 30 of main body portion 24 by valve member 50 which is held in its seated relation to beveled annular surface 52 by spring member 46 which in turn is supported by annular shelf means 48 formed in cavity 42 of the projecting portion 36 of base member 38 as aforesaid.

Water travels through passageway 54 into tube 56, wand 60 and out nozzle 62; the user directs the jet stream of water emanating from nozzle 62 to the spaces between the teeth and to the gums as well. If the pressure of the water in cavity 26 is too high, the resistance of spring 46 is overcome and valve member 50 separates from its seated relation to beveled annular surface 52 and water flows through cavities 42 and 44 of base member 38 into the sink basin; it should be understood, however, that water, at lower pressure, will continue to flow from nozzle 62 even when valve member 50 is unseated.

It is also important to note that the pressure at which the valve 50 will be unseated is preselected by rotating base member 38 relative to main body portion 24, i.e., counterclockwise rotation of base member 38 relative to main body portion 24 of device 10 lowers the force exerted by spring 46 against valve 50 and thus lowers the threshold pressure at which valve 50 will unseat. Clockwise rotation of base member 38 has the opposite effect.

The quick release means whereby device 10 is attached and detached to and from adapter 12, respectively, will now be described.

The annular uppermost portion 64 of main body member 24 is slotted as at 66, 68. As perhaps best shown in FIG. 2, flexible arm members 70, 72 of a generally "U"-shaped retaining clip member 74 have an obtuse angle bend formed therein as shown and are received in slots 66, 68, respectively, when the retaining clip 74 is in its equilibrium position.

Figure 2:
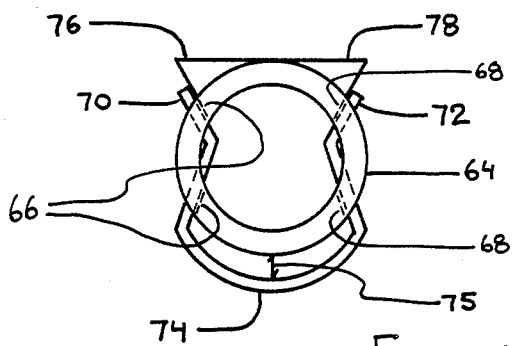
FIG. 2 is a top plan view of the mechanism that maintains the device in secured relation to a faucet when water is entering the device.

When retaining clip 74 is in its equilibrium position, it is spaced as at 75 from the upper portion 64 of main body portion 24 of the novel device as shown in FIG. 2.

As perhaps best understood by comparing FIGS. 1 and 2, when flexible arm members 70, 72 of retaining clip 74 are disposed within their respective slot means 66, 68, as shown in FIG. 2, said flexible arm members 70, 72 will overlie annular flange member 20 formed in adapter 12 and will thus prevent separation of main body portion 24 of device 10 from adapter 12. In other words, in the absence of retainer member 74 and its arms 70, 72, water from faucet 18 entering cavity 26 of main body member 24 could cause main body 24 to separate from adapter 12. Arms 70, 72 of retaining clip 74, since they overlie annular flange 20 of adapter means 12 when the device 10 is fully assembled, prevent such separation when arms 70, 72 are in their equilibrium position as shown in FIG. 2.

Figure 3:
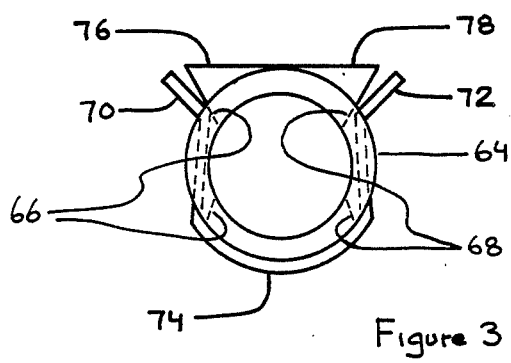
FIG. 3 is a plan view of the parts shown in FIG. 2, but showing the relative positioning of parts when the device is separable from a faucet.

However, after the device has been used, it will be desired to separate it from adapter 12 and return it to its support surface. Thus, retaining clip 74 is pressed against the upper portion 64 of main body portion 24, as shown in FIG. 3, thereby deleting space 75 which appears in FIG. 2. The FIG. 3 position of clip 74 is its non-equilibrium position. The leading edges of flexible arms 70, 72 now abut wedge shaped means 76, 78, respectively, that are integral with the upper portion 64 of main body portion 24 as shown in FIG. 3. The wedging action of wedge means 76 and 78 drives the bent portion of arms 70, 72 out of slots 66, 68 as clearly shown in FIG. 3. This allows main body portion 24 to be moved downwardly so that it is disengaged from adapter member 12 without interference between annular flange member 20 and the flexible arm members 70, 72 of retaining clip 74.

Figure 6:
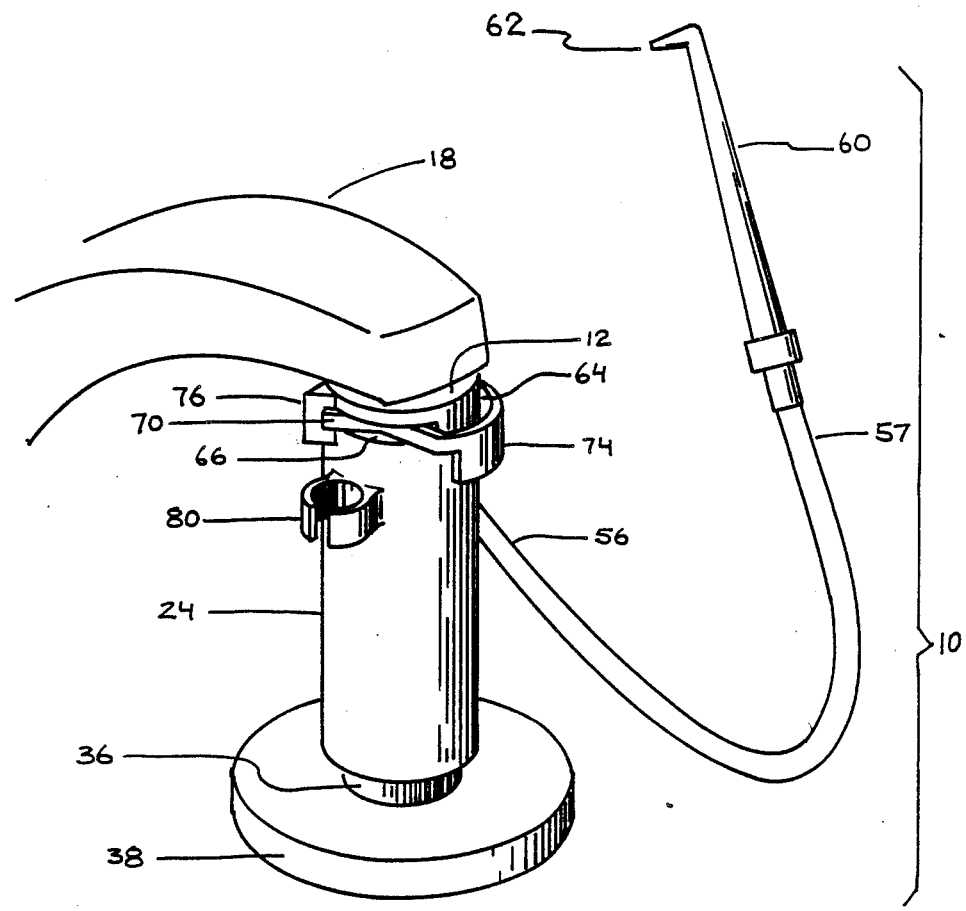
FIG. 6 is a perspective view of the assembled invention.

When clip 74 is released, it resumes its FIG. 2 position; the equilibrium position of clip 74 is also depicted in FIG. 6.

Figure 4:
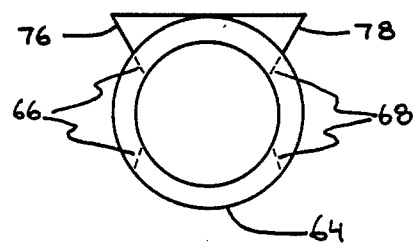
FIG. 4 is a plan view of one of the parts of FIGS. 2 and 3 in isolation.
Figure 5:
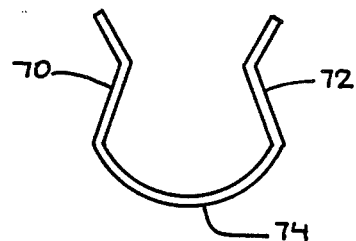
FIG. 5 is a plan view of the other of the two parts shown in FIGS. 2 and 3.

FIGS. 4 and 5 show the upper portion 64 of main body member 24 and retaining clip 74 individually to further clarify FIGS. 1–3.

FIG. 6 depicts the assembled device secured to faucet 18, in its equilibrium position as aforesaid. As suggested in FIG. 6, wand 60 may be stored on clip 80 when the device is not in use.

INDUSTRIAL APPLICABILITY

Those skilled in the art of water dispensing oral hygiene devices will recognize the invention disclosed herein as representing a major advance in the art. Among its many features and advantages are its quick attachability and releasability, its adjustable over-pressure relief means, and its ability to support itself on a substantially level surface in a free-standing configuration. The novel retaining clip 74 and its bent arms 70, 72 which are driven from slots 66, 68 due to the wedging action of member 76, 78 when the clip is depressed by the user's thumb, is also highly novel. This invention makes a significant contribution to the dental hygiene industry.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A dental hygiene device that directs water from a faucet onto dental surfaces, comprising:
   a hand-held wand member;
   a water-emitting nozzle means formed in said wand member;
   a fluidic device having a water-receiving first end and a water-discharging second end;
   an over-pressure relief valve means for opening said second end when water pressure inside said fluidic device is above a predetermined threshold pressure;
   a bore means formed in said fluidic device between its first end and its second end;
   an elongate, flexible conduit means that provides fluid communication between said fluidic device and said wand member;
   an adapter means having a first end substantially permanently secured to a discharge spout of a faucet and a second end releasably secured to said fluidic device;
   a quick release means, having an equilibrium state and a non-equilibrium state, that releases said first end of said fluidic device from said adapter means quickly when in its non-equilibrium state and which securely retains said fluidic device to said adapter means when in its equilibrium state; and
   said quick release means being a generally "U"-shaped retaining clip member having a pair of transversely spaced apart, flexible arm members, and wherein each arm member has an obtuse angle bend formed therein.

2. The device of claim 1, further comprising adjustment means for preselecting the pressure at which said over-pressure relief valve mans opens.

3. The device of claim 2, wherein said fluidic device includes a tubular main body portion, wherein an upper portion of said main body portion slidingly receives said adapter means therein when the device is assembled, and wherein said quick release means includes means engaging said adapter means and retaining it within said upper portion when said quick release means is in its equilibrium state.

4. The device of claim 3, wherein said adapter means includes an annular flange member that is engaged by said quick release means when said quick release means is in its equilibrium state.

5. The device of claim 4, where said upper portion has a pair of slot means formed therein, on opposite sides thereof.

6. The device of claim 5, wherein each of said arm members is positioned within a different slot means of said pair of slot means when said quick release means is in its equilibrium position, and wherein when said arm members are so positioned, said arm members overlie opposite portions of said adapter means annular flange member and thus prevent separation of said fluidic device main body portion from said adapter means.

7. The device of claim 6, further comprising means for causing said arm members to diverge with respect to one another and to thereby substantially withdraw from their respective positions within said slot means when said quick release means is not in its equilibrium position.

8. The device of claim 7, wherein said means for causing said arm members to diverge includes, at least in part, a pair of transversely spaced apart wedge members formed integral to said fluidic device and positioned forwardly of respective distal free ends of said arm members.

9. The device of claim 8, wherein said arm members are sufficiently elongate to position said retaining clip member in spaced relation to said fluidic device when said arm members are positioned within said slot means, whereby depressing said retaining clip member causes it to abut the fluidic device, in which position the arm members of said retaining clip member are driven out of their respective slot means by said wedge members so that said adapter means and said fluidic device may be separated.

10. The device of claim 9, further comprising a substantially flat-bottomed base means that supports said fluidic device in free-standing relation to a substantially level support service when said device is separated from said adapter means.

11. The device of claim 10, wherein said pressure relief valve means includes a biased valve member that is unseated only when water pressure within said fluidic device exceeds a predetermined threshold.

12. The device of claim 11, wherein said base means includes an integral, upstanding sleeve member that receives and supports a lower end of a biasing means that loads said biased valve member.

13. The device of claim 12, wherein said, main body portion and said sleeve member are screw threadedly engaged so that relative rotation therebetween provides said adjustment means.

14. The device of claim 13, further comprising a wand support member fixedly secured to an exterior sidewall of said fluidic device so that said wand member is supported thereby when not in use.

* * * * *